(12) United States Patent
Weber et al.

(10) Patent No.: US 9,901,548 B2
(45) Date of Patent: Feb. 27, 2018

(54) COMPOSITIONS FOR ENCAPSULATING BIOMATERIALS AND USES RELATED THERETO

(75) Inventors: Collin J. Weber, Atlanta, GA (US); Susan A. Safley, Decatur, GA (US); Kereen S. Gordon, Alpharetta, GA (US); Nicholas E. Simpson, Alachua, FL (US)

(73) Assignee: EMORY UNIVERSITY, Atlanta, GA (US)

( * ) Notice: Subject to any disclaimer, the term of this patent is extended or adjusted under 35 U.S.C. 154(b) by 0 days.

(21) Appl. No.: 14/000,471

(22) PCT Filed: Mar. 14, 2012

(86) PCT No.: PCT/US2012/029049
§ 371 (c)(1),
(2), (4) Date: Dec. 30, 2013

(87) PCT Pub. No.: WO2012/129024
PCT Pub. Date: Sep. 27, 2012

(65) Prior Publication Data
US 2014/0105974 A1    Apr. 17, 2014

Related U.S. Application Data

(60) Provisional application No. 61/454,160, filed on Mar. 18, 2011.

(51) Int. Cl.
*A61K 9/48* (2006.01)
*A61K 35/39* (2015.01)
*A61K 47/69* (2017.01)

(52) U.S. Cl.
CPC ............ *A61K 9/4891* (2013.01); *A61K 35/39* (2013.01); *A61K 47/6925* (2017.08)

(58) Field of Classification Search
None
See application file for complete search history.

(56) References Cited

U.S. PATENT DOCUMENTS

| | | | |
|---|---|---|---|
| 4,689,293 A | 8/1987 | Goosen | |
| 5,084,350 A | 1/1992 | Chang | |
| 5,227,298 A | 7/1993 | Weber | |
| 5,578,314 A | 11/1996 | Cochrum | |
| 5,795,570 A * | 8/1998 | Weber et al. | 424/93.7 |
| 5,858,746 A | 1/1999 | Hubbel | |
| 5,876,742 A * | 3/1999 | Cochrum et al. | 424/424 |
| 7,824,672 B2 | 11/2010 | Chaikof | |
| 2004/0047890 A1 | 3/2004 | Weber | |
| 2010/0172942 A1 | 7/2010 | Wang | |

FOREIGN PATENT DOCUMENTS

WO    2008011518    1/2008

OTHER PUBLICATIONS

Steurer et al., Ex Vivo Coating of Islet Cell Allografts with Murine CTLA4/Fc Promotes Graft Tolerance, Journal of Immunology, 1995, 155:1165-1174.*
Calafiore et al., Alginate microcapsules for pancreatic islet cell graft immunoprotection: struggle and progress towards the final cure for type 1 diabetes mellitus, Expert Opinion on Biological Therapy (2003) vol. 3 (No. 2): pp. 201-205.*
Thu et al., Alginate polycation microcapsules. I. Interaction between alginate and polycation, Biomaterials, 1996, 17 (10):1031-40.
Vos et al., Alginate-based microcapsules for immunoisolation of pancreatic islets, Biomaterials 27 (2006) 5603-5617.
NISCO Engineering, Encapsulation Unit—VAR V1.
Narang et al. Biological and Biomaterial Approaches for Improved Islet Transplantation Pharmacol Rev, 58:194-243, 2006.
Safley et al. Biocompatibility and Immune Acceptance of Adult Porcine Islets Transplanted Intraperitoneally in Diabetic NOD Mice in Calcium Alginate Poly-L-lysine Microcapsules versus Barium Alginate Microcapsules without Poly-L-lysine Journal of Diabetes Science and Technology vol. 2, Issue 5, 2008, 760-67.
Cui et al. Long-term metabolic control of autoimmune diabetes in spontaneously diabetic nonobese diabetic mice by nonvascularized microencapsulated adult porcine islets. Transplantation. 2009;88(2):160-169.
Extended European Search Report, 2015.
Calafiore, Alginate microcapsules for pancreatic islet cell graft immunoprotection: struggle and progress towards the final cure for type 1 diabetes mellitus, 2003, Expert Opinion on Biological Therapy, 3:2, 201-205.
Orive et al. Biocompatibility of alginate-poly-L-lysine microcapsules for cell therapy, Biomaterials 27 (2006) 3691-3700.

* cited by examiner

*Primary Examiner* — Thane Underdahl
*Assistant Examiner* — Evelyn Y Pyla
(74) *Attorney, Agent, or Firm* — Emory Patent Group

(57) ABSTRACT

This disclosure relates to compositions and methods for encapsulating biomaterials such as cells to prevent immune responses. In certain embodiments, the disclosure relates to capsules comprising a cell or cells gelled in alginate coated with a layer that prevents migration of immune molecules to the cell surface and an outer capsule layer comprising non-immunogenic material optionally containing immunosuppressive agents. In certain embodiments, the cells are capable of generating insulin that emanates from the capsule.

2 Claims, 8 Drawing Sheets

COMPOSITIONS FOR ENCAPSULATING BIOMATERIALS AND USES RELATED THERETO

CROSS REFERENCE TO RELATED APPLICATIONS

This Application is a National Stage entry and claims priority to International Application Number PCT/US12/29049 filed 14 Mar. 2012 and U.S. Provisional Application No. 61/454,160, filed Mar. 18, 2001, both hereby incorporated by reference in their entirety.

BACKGROUND

Pancreas transplantation can benefit a person with type 1 diabetes with severe, frequent hypoglycemia. An alternative treatment is the transplantation of the insulin producing cells, isolated islets. These methods are limited due to the scarcity of pancreas and islets for donation. Rejection of the transplanted pancreas or islets from a donor is inevitable without co-administration of immunosuppressive agents. Immunosuppressive therapies also often results in undesirable side effects. Minimizing the amount of agents needed for suppression can significantly improve the living conditions of the subject. Thus, there is a need to identify improved therapeutic alternatives.

Adult porcine islet (API) xenografts are an alternate source of donor cells. Such a strategy is promising because transplantation of microencapsulated islet xenografts restores normoglycemia in nonobese diabetic (NOD) mice. Various immunoisolation strategies, including alginate microcapsules, have been reported to protect discordant islet xenografts from rejection for short periods. Chang et al., U.S. Pat. No. 5,084,350 describe the microencapsulation of biological materials using gels. Safley et al., J Diab Sci Tech, 2008, 2: 760, disclose adult porcine islets in calcium alginate poly-1-lysine (PLL) microcapsules. Unfortunately, certain alginate PLL microcapsules are not durable long-term. See also Cui et al., Transplantation, 2009, 88(2):160-169, U.S. Pat. Nos. 5,227,298, and 5,795,570. Thus, there is a need to identify improved vehicles.

SUMMARY

This disclosure relates to compositions and methods for encapsulating biomaterials such as cells to prevent immune responses. In certain embodiments, the disclosure relates to capsules comprising a cell or cells gelled in alginate coated with a layer that prevents migration of immune molecules to the cell surface and an outer capsule layer comprising non-immunogenic material optionally containing immunosuppressive agents. In certain embodiments, the cells are capable of generating insulin that emanates from the capsule.

In certain embodiments, the disclosure relates to capsules comprising: a) a cell; b) an anionic polysaccharide; c) a cation; wherein the cell is surrounded by a first layer comprising the anionic polysaccharide and the cation; wherein the first layer is surrounded by second layer comprising a anionic polysaccharide and a cation; and wherein a third layer comprising a protein blocking polymer configured between the first and second layers. In certain embodiments, the cell is an insulin producing cell such as an islet cell. In certain embodiments, the protein blocking polymer comprises monomers with amine groups such as poly-lysine or poly-glucosamine.

In certain embodiments, the anionic polysaccharide is an alginate. In certain embodiments, the alginate in the first and second layer is a LVG or LVM alginate. In certain embodiments, the second layer comprises alginate, a cation, and G-blocks. In certain embodiments, the anion polysaccharide in the first layer and the second layer is an alginate wherein the concentration of alginate in the first layer is greater than in the second layer. In certain embodiments, the cation in the second layer is strontium. In certain embodiments, the first layer is less than 3.5% low viscosity alginate by weight and the second layer is about 2% low viscosity alginate by weight. In certain embodiments, the capsule is between about or greater than 400 or 500 μm to 1500 μm. In certain embodiments, the diameter of the capsule is more than 400 or 500 micrometers.

In certain embodiments, the second layer further comprises an immunosuppressive agent. In certain embodiments, the immunosuppressive agent is a fusion protein composed of the Fc fragment of a human IgG immunoglobulin linked to the extracellular domain of CTLA-4.

In certain embodiments, the first layer may comprise an insulin producing cell and a stem cell such as a mesenchymal stem cell.

In certain embodiments, the first layer may comprise a stem cell optionally in combination with an insulin producing cell, such as an islet cell.

In certain embodiments, the anionic polysaccharide is an alginate. In certain embodiments, the alginate has a low endotoxin concentration (<50 EU/g), a low viscosity (<60 mPa), or high mannuronic acid (>50%) alginate. In certain embodiments, the cation is a calcium, barium, or strontium cation.

In certain embodiments, the second layer comprises polysaccharide crosslinkers.

In certain embodiments, the disclosure relates to methods of treating diabetes comprising implanting a capsule as disclosed herein in a human subject diagnosed with diabetes and optionally administering an immunosuppressive agent to the subject.

In certain embodiments, the disclosure relates to the use of a capsule disclosed herein in the production of a medicament for the treatment or prevention of diabetes.

In certain embodiments, the disclosure relates to methods of producing compositions disclosed herein by mixing the starting materials under conditions such that the products are formed. In certain embodiments, the disclosure relates to the products produced by these processes.

DETAILED DISCUSSION

Figure 1:
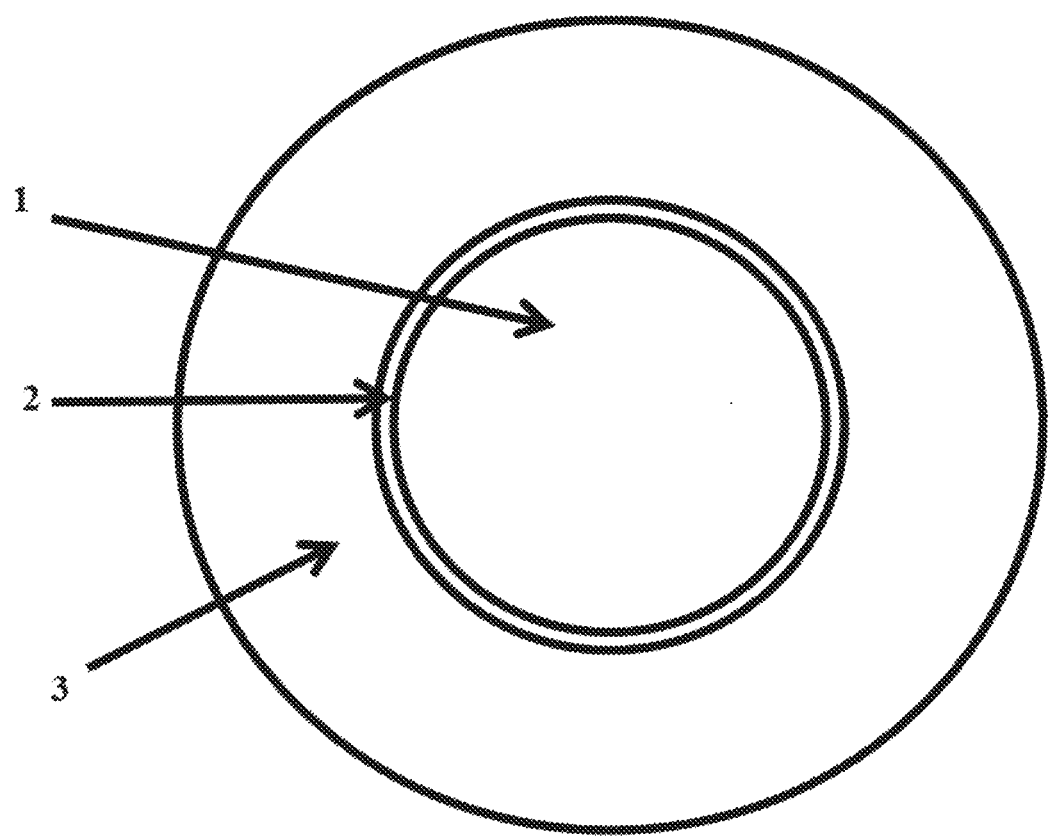
FIG. 1 illustrates certain embodiments of the disclosure. This embodiment of a capsule contains an inner layer (1) of Ca-gelled LVG or LVM alginate containing an islet cell coated with multiple layers (2) of either PLL or chitosan to confer permselectivity (<150 kDa), and re-encapsulated in another layer (3) of Sr-gelled LVM alginate to conceal the PLL/chitosan layer(s) (2), to enhance durability. The outer layer (3) optionally contains immunosuppressant agents, such as CTLA4-Ig, anti-CD154 mAb, and immunosuppressive cytokines.

This disclosure relates to compositions and methods for encapsulating biomaterials such as cells to prevent immune responses. In certain embodiments, the disclosure relates to capsules comprising a cell or cells gelled in alginate coated with a layer that prevents migration immune molecules to the cell surface and an outer capsule layer comprising non-immunogenic material optionally containing immuno-suppressive agents. In certain embodiments, the cells are capable of generating insulin that emanates from the capsule.

In one embodiment, a double capsule is comprised of an inner capsule coated with PLL to exclude IgG that is then re-encapsulated to conceal the PLL in a more dilute alginate cross-linked with strontium for durability.

In certain embodiments, it is an object of the disclosure to provide a capsule that improves the immunoprotection of xenogeneic donor islets and delivers tolerogenic factors to the islet recipient.

In certain embodiments, it is an object of the disclosure to provide capsules that allow a reduction of the extent of immunosuppression when implanted with encapsulated insulin producing cells. This allows one to reduce the amount immunosuppressive drugs needed to prevent rejection and thereby reducing the side effects immunosuppressive drug have on the subject.

In certain embodiments, it is an object of the disclosure is to provide capsules that promote optimal metabolic control of glucose by islet allografts or xenografts.

Disclosed herein is a double microcapsule containing an insulin producing cell which as the following improved properties—it excludes IgG from contacting the inner layer comprising the insulin producing cell and functions with normoglycemia when transplanted in a subject. This is significant because non-human primate (NHP) and human serum (containing IgG and complement) will lyse islets in vitro, and the double capsule prevents injury of islets by NHP serum in vitro.

Terms

The term "anionic polysaccharide" refers to a polysaccharide comprising sugar monomers with carboxylic acid groups, e.g., alginates. Mannuronate and guluronate contain a carboxylic acid group. The term "alginate" refers to a copolymer with polymeric blocks of (1-4)-linked β-D-mannuronate (M) and its C-5 epimer, α-L-guluronate (G) residues, respectively. The monomers may be covalently linked together in different sequences or blocks. The monomers can appear in homopolymeric blocks of consecutive G-residues (G-blocks), consecutive M-residues (M-blocks) or alternating M and G-residues (MG-blocks), or combinations thereof.

Alginate is typically extracted from marine algae (seaweed). Alginate is present in the cell walls of brown algae as the calcium, magnesium and sodium salts of alginic acid. The calcium and magnesium salts do not dissolve in water; the sodium salt does. The rationale behind the extraction of alginate from the seaweed is to convert the alginate salts to the sodium salt, dissolve this in water, and remove the seaweed residue by filtration. The alginate may then be recovered from the aqueous solution. Sargassum usually gives a lower viscosity alginate. Seaweed is colored, and the alkaline extract will also be colored. Color can be controlled by the use of bleach—sodium hypochlorite. Bleaching can lower the viscosity of the alginate. Bleaching alginate may change the molecular weight and make minor structural modifications. The term is intended to include such modified forms.

The term "LVG" refers to a low viscosity alginate, i.e., of less than 200 mPas, typically 20 to 200 mPas, wherein more than half of the monomer units are guluronate, typically more than 60%. The term "LVM" refers to a low viscosity alginate wherein more than half of the monomer units are mannuronate. The term "MVG" refers medium viscosity alginate, i.e., greater than 200 mPas wherein more than half of the monomer units are guluronate, typically more than 60%. The apparent viscosity is measured in 1% (w/w) sodium alginate solution at 20° C. using Brookfield viscosimeter at 20 rpm.

The carboxylic acid groups can be deprotonated in a solution of sufficient pH forming the carboxy anion. Mannuronate and guluronate contain a carboxylic acid group that can act as a ligand to cations such as metal cations, e.g., sodium, calcium, barium, strontium. The pKa values for mannuronic and guluronic acid are 3.38 and 3.65, respectively. Capsules may be prepared by forming a drop of an alginate and water gel and exposing the gel to a buffered solution containing a cationic salt; however other methods are contemplated.

It certain contexts, this disclosure refers to a percentage of alginate which refers to the percentage by weight of sodium alginate in a volume of water optionally including salts used in the process of creating the initial capsule or added layers. For example, 3.0 grams of sodium alginate added to 100 mL of water of 1% sodium chloride solution would be 3.0% alginate by weight. The actual volume of alginate water solution may be closer to about 103 mL due to the added volume of the alginate in the water. The actual capsule may contain more or less alginate by percentage due to hydration or dehydration during the curing process with the cationic salts.

The term, "immunosuppressant" refers to any of a variety of agents that suppresses or reduces an adaptive or innate immune response, e.g., suppresses or reduces activation of T-cells, B-cells, or neutrophils. The immunosuppressive agent may be a drug, polypeptide, antibody, or a polysaccharide that suppresses a T-cell response. Specifically contemplated immuno-suppressants are proteins and antibodies that interrupt signaling between these molecules such as CTL4 (Cytotoxic T-Lymphocyte Antigen 4) which transmits an inhibitory signal to T-cells by binding B7. The immunosuppressive agent may be a fusion protein composed of the Fc fragment of a human Ig immunoglobulin, e.g., IgG linked to the extracellular domain of CTLA-4. In certain embodiments, the immunosuppressive agent is selected from the group consisting of abatacept, belatacept, alefacept, antibody to lymphocyte function-associated antigen 1 (TS-1), antibody to CD40, an antibody to CD154, a non-depleting anti-CD4 monoclonal antibody (YTS177.9), muromonab-CD3, ciclosporin, tacrolimus, rapamycin, voclosporin, Arg-Gly-Asp (RGD) peptide, T-cell receptor directed antibodies, IL-2 receptor directed antibodies, anti-CD20. The term is intended to encompass anti-inflammatory agents such as aspirin, acetaminophen, NSAIDs, TNF alpha antibodies like infliximab, adalimumab, or certolizumab pegol, or fusion proteins like etanercept.

EXPERIMENTAL

Example 1: Double Capsules

Double capsules were successfully made using the formulations shown in Table 1

TABLE 1

Formulation of Double Capsules, size in micrometers (μm).

| | Inner | | | | Outer | | | | |
|---|---|---|---|---|---|---|---|---|---|
| Alginate | Conc | Cation | PLL Layer | Size | Alginate | Conc | Cation | PLL Layer | Size |
| LVM | 3.2% | Ca | 1 | 500-700 | MVM* | 1.30% | Sr | 0 | 1000-1200 |
| LVM | 3.2% | Ca | 1 | 500-700 | LVM | 2% | Sr | 0 | 1000-1200 |

Figure 2:
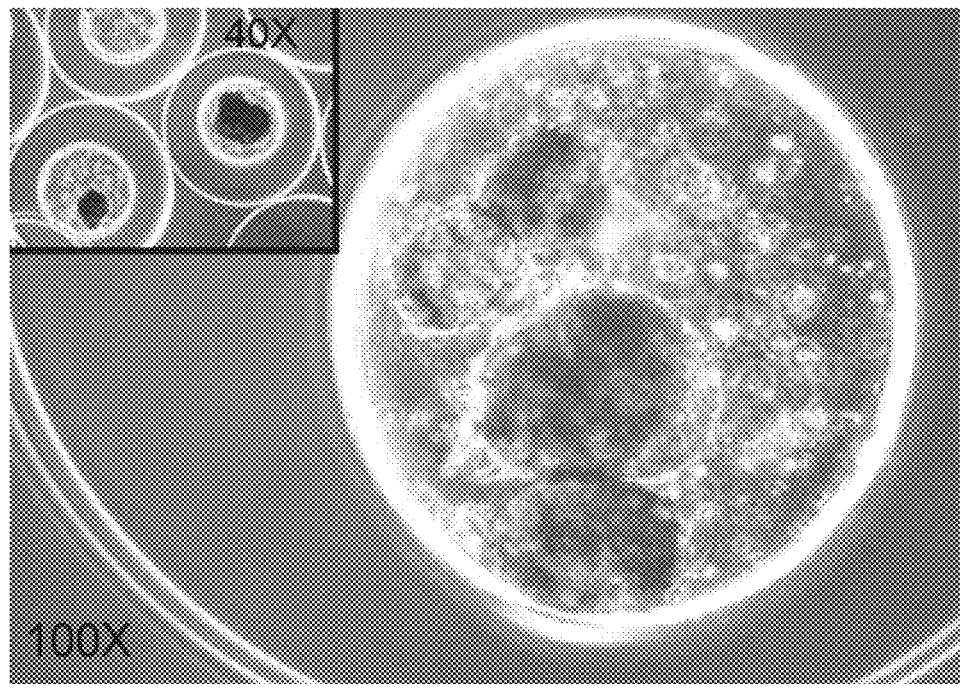
FIG. 2 shows pictures of porcine islets in double capsules illustrated in FIG. 1 (100×, phase contrast). Inset=40× phase contrast.

The concentration of alginate in the outer layer is substantially less than the concentration of the alginate in the inner bead, or the inner bead collapses. One layer of PLL inhibits the diffusion of IgG into the inner bead as well as 2-4 layers of PLL. In order for the outer capsule to form properly, it is important to use as high a concentration of alginate as possible without causing the inner bead to collapse (for example, about 2% for the outer alginate layer, when the inner bead is about 3.2% alginate). For successful re-encapsulation, at least an 8:1 volume of alginate: small capsules may be used. Finally, the data shows that Sr can be substituted for Ca when gelling the outer layer. After carefully testing numerous conditions, a durable, immunoprotective double capsules can be made with a 3.2% Ca-gelled 500-700 um inner bead coated with 1 layer of PLL, re-encapsulated in Sr gelled 2% LVM (Table 1). This capsule was used for transplanting islets in diabetic NOD and NOD-scid mice. See FIGS. 2 and 3A and 3B.

The double capsules shown in Table 1 were based on studies of single capsules, as shown in Table 2.

TABLE 2

Effects of M vs G alginate, alginate concentration, addition of G blocks, and number of PLL layers on diffusion of IgG into single capsules, size in micrometers

| Alginate | Conc | Capsule diameter (mM) | G Blocks | Cation | # PLL Layers | Permeable to IgG? |
|---|---|---|---|---|---|---|
| LVG* | 2.9% | 800-900 | Yes (5%) | Sr | 0 | Yes |
| LVG | 2.9% | 800-900 | Yes (5%) | Sr | 1 | No |
| LVG | 2.9% | 800-900 | Yes (5%) | Sr | 2 | No |
| LVG | 2.9% | 800-900 | Yes (5%) | Sr | 3 | No |
| LVG | 2.9% | 800-900 | Yes (5%) | Sr | 4 | No |
| LVM* | 2% | 200-400 | Yes (5%) | Ca | 1 | Inner bead collapsed with PLL |
| LVM | 2% | 200-400 | No | Ca | 1 | |
| LVM | 2% | 800-900 | No | Ca | 0 | Yes |
| LVM | 2% | 800-900 | No | Ca | 1 | No |
| LVM | 3.3% | 800-900 | No | Ba | 0 | Yes |
| LVM | 3.3% | 800-900 | No | Ca | 0 | Yes |
| LVM | 3.3% | 800-900 | No | Ca | 2 | No |
| LVM | 3.3% | 800-900 | Yes (5%) | Ca | 4 | No |
| LVM | 3.5% | 400-700 | No | Ca | 1 | Too viscous to form beads |

These studies indicated that: (1) small (200-400 um) capsules collapsed when coated with PLL, (2) IgG diffused into standard Ba-gelled 3.3% LVM alginate capsules without PLL, (3) IgG diffused into 2.9% Sr-gelled LVG capsules with G blocks, but PLL coating prevented it, (5) IgG diffused into 2% and 3.3% Ca-gelled LVM capsules, but PLL coating prevented it, (6) the addition of 5% G blocks to 2.9% LVG lowered the apparent viscosity of the alginate, and (7) a relatively high concentration (i.e. 3.5%) of a relatively viscous alginate did not make uniformly formed, round capsules.

Example 2: Double Encapsulation Method

Reagents and solutions: 1.1% $CaCl_2$ solution—Dissolve 14.7 g Calcium Chloride dehydrate (Sigma Aldrich, St. Louis, Mo.) (MW 147.02) and 46 g D-mannitol (Sigma Aldrich, St. Louis, Mo.) (MW 182.17) in ultrapure $dH_2O$ with 25 mM HEPES (Hyclone Laboratories, Logan Utah), adjust pH to 7.4, and bring the volume up to 1 L with HEPES-buffered $dH_2O$.

100 mM $SrCl_2$—Dissolve 26.6 g Strontium Chloride hexahydrate (Sigma Aldrich, St. Louis, Mo.) (MW 266.62) and 4.6% D-mannitol in HEPES-buffered $dH_2O$. Adjust pH to 7.4. Bring the volume up to 1 L with HEPES-buffered $dH_2O$.

0.1% CHES (Sigma Aldrich, St. Louis, Mo.)—Mix 25 ml of 2% CHES, pH 8.2, with a 1.1% $CaCl_2$ to make a 0.1% CHES solution.

Poly-L-lysine (PLL) (Sigma Aldrich, St. Louis, Mo.)—Dissolve 0.05 g PLL in 100 ml of 0.9% $NaCl_2$ solution by swirling gently. Sterile filter using a 0.22 µm Millipore filter unit.

Encapsulation Devices—16 gauge angio-cath unit (BD ref #381157); Extension set 30 inches (Abbot Labs 4610); Silicone tubing for peristaltic pump, polyvinyl chloride, 14 inches long, pkg of 12, Cat. #39625, 1.52 mm ID, max flow 8.3 ml/min; Tubing connector (2 per set-up needed) Cole-Palmer 2-047-009-03-0; Medical silicone tubing Baxter T5715-7 or Helix Medical Tubing ref 60-011-07 size: 0.062" ID/0.095" OD 1.58 mmID/2.41 mm OD.

Procedure: Cut the extension tubing as follows, the male end to 7 inch length and the female end to 6 inches in length. Discard the center section. Remove the needle from the catheter unit. Discard needle in sharps container. Keep the plastic sheath that covered the needle. Firmly attach the male end of the tubing into connector of the catheter sheath. Attach tubing connector to other end of the extension tubing. Attach peristaltic tubing (yellow collar end) to a tubing connector. Attach blue collar end of peristaltic tubing to another tubing connector. Cut silastic tubing to 6 inch length. Attach to another tubing connector and to top of needle unit. Attach cut end of female extension unit to needle air port. Insert male end of air filter into female end of tubing. Place unit into sealable sterilizing bag, insert indicator strip. Seal bag. Make sure that there are no kinks in the silastic tubing, as this can impede liquid flow.

Encapsulation procedure: Prepare inner alginate microcapsules—Dissolve UP LVM sodium alginate (Nova Matrix, Oslo, Norway)(for example, having a mannuronic acid content of 59%), in 0.9% Sodium Chloride (Baxter Healthcare Corporation, Deerfield, Ill.), 3.2% w/v, and stir overnight at room temperature. Suspend adult porcine islets (APIs) in alginate solution (20,000 IEQ APIs/mL alginate) in a sterile 15 cc or 50 cc conical tube. Attach the conical tube with islet/alginate suspension a Dynamax® peristaltic pump using the encapsulation device as described below:

Sanitize the hood area by spraying with a 70% ethanol spray bottle and wiping clean. Check adjustment of the side arm clamp on the ring-stand. The desired location of the side arm clamp should be directly above a sterile 1 liter beaker placed on the surface of the hood. Aseptically unseal the encapsulation device, making sure not to contaminate the sheath opening. Place the 15 ml conical tube containing the islet/alginate mixture in a rack next to the pump. Position the encapsulation needle housing above the beaker. Set the pump to 2 mL/min, with airflow 6 liters/minute. Add 100 mL of 1.1% mM 4.6% mannitol $CaCl_2$ solution to the beaker. Position the tubing from the 15 ml conical tube with islet/alginate mixture in the peristaltic pump, make sure the encapsulation needle is properly positioned above the beaker, and start the pump.

After all the islet/alginate suspension has passed through the needle, stop the pump. Collect the capsules in a 50 ml conical tube and allow gelling for 10 minutes in the 4.6% mannitol $CaCl_2$ solution on a rotator. Wash the microcapsules by allowing capsules to settle to the bottom of the tube, aspirating the buffer, then adding the next wash solution. After washing in 0.1% CHES, followed by a wash in 1.1% $CaCl_2$, add 0.05% PLL solution and incubate for the capsules for 10 minutes on a rotator. Wash the capsules.

Culturing of PLL-coated capsules—PLL-coated encapsulated islets can be cultured for up to three days before they are re-encapsulated. PLL coated encapsulated islets should be cultured in Medium E199 culture medium (CELLGRO®, Mediatech, Manassas, Va.) supplemented with 25 mM HEPES, 10% w/v porcine serum (Sigma Aldrich, St. Louis Mo.), 20 µg/ml ciprofloxacin (Sigma Aldrich), 2 mM L-Glutamine (CELLGRO®, Mediatech), 100 IU/ml of penicillin and 50 to 100 (ug/ml) streptomycin (CELLGRO®, Mediatech). On day 3, they can be re-encapsulated.

Double Encapsulation procedure: Prepare the outer alginate microcapsules as follows: Dissolve UP LVM sodium alginate (Nova Matrix, Oslo, Norway) (for example, with a mannuronic acid content of 59%) in 0.9% Sodium Chloride (Baxter Healthcare Corporation, Deerfield, Ill.) 2.0% w/v and stir overnight at room temperature. Mix the inner microcapsules with 2.0% sterile alginate at a ratio of 1 ml of beads to 8 mL of alginate. The beads and alginate should be thoroughly mixed and poured into a syringe. The electrostatic bead generator is used to re-encapsulate the inner beads in alginate. Attach the syringe to sterile extension tubing (about 6 inches). Then attach the extension tubing to silicone tubing (about 10 inches). Then attach the silicone tubing to the encapsulation needle (nozzle) which is supported by the nozzle holder unit of the electrostatic bead generator. Gently mix the alginate/bead so that the beads are well distributed. Install the syringe in a Harvard apparatus syringe pump which is mounted onto a Nisco electrostatic bead generator. The voltage of the electrostatic bead generator should be adjusted to 9 kV, with a flow rate of 10 ml/hr (if using a 1.2 mm Nisco needle). Extrude the alginate/bead mixture through a 1.2 mm Nisco needle into a sterile beaker containing 50 mM $SrCl_2$ (50 mL) and a small stir bar. Place the beaker on the magnetic agitator within the bead generator, in order to gently mix the capsules with the $SrCl_2$. Collect the double capsules in a 50 ml conical tube, allow to gel 10-20 minutes without rotation, and wash.

Figure 3A:
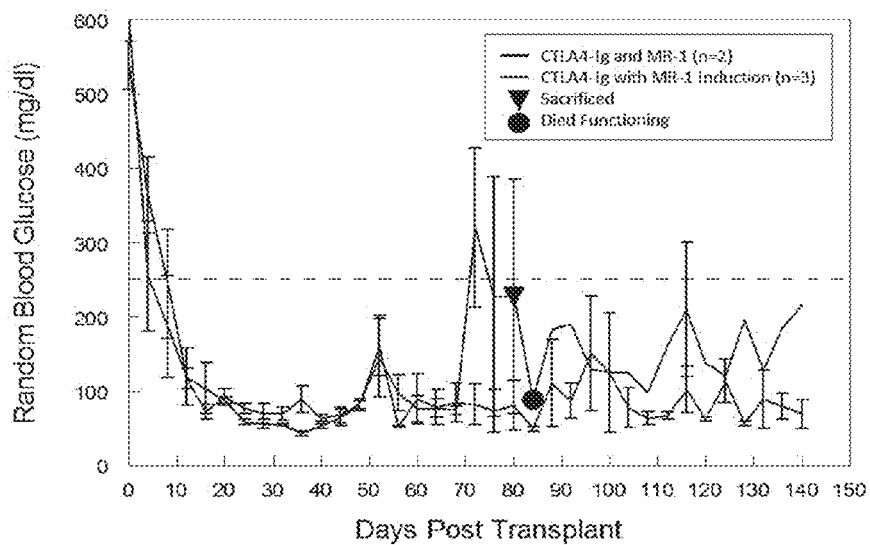
FIG. 3A shows function of APIs in double capsules in NODs treated with CTLA4-Ig and MR1 or when MR1 therapy is withdrawn after 1 week ("induction").
Figure 3B:
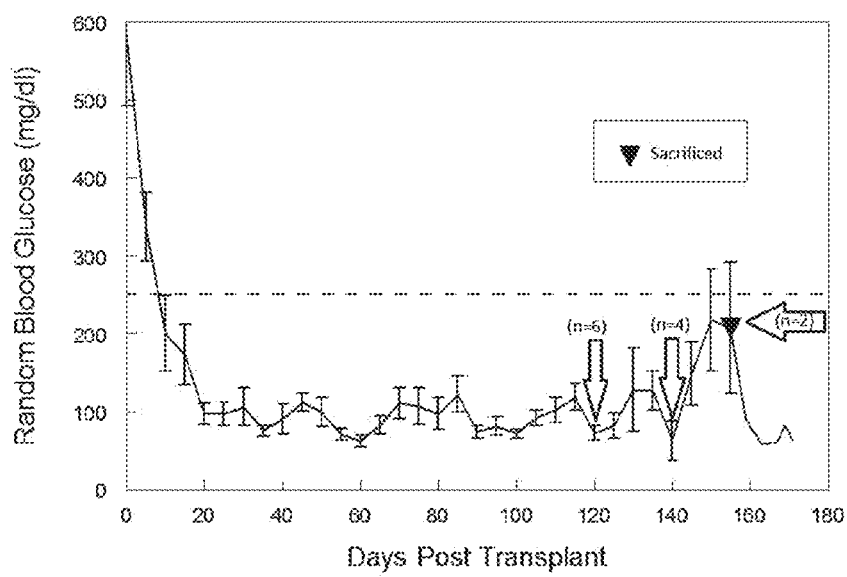
FIG. 3B shows function of APIs in double capsules in NODs treated with a single agent, YTS177.9 (a non-depleting anti-CD4 monoclonal antibody).

Example 3: Double Capsules Containing Adult Porcine Islets (APIs) Transplanted into Mice Double capsules containing APIs have been transplanted into spontaneously diabetic NOD mice (given continuous costimulatory blockade [CTLA4-Ig and MR1] versus continuous CTLA4-Ig and MR1 induction [one week]. The grafts are functioning on day 140 post-transplant in NOD mice receiving costimulatory blockade (n=2) and in 1 of 3 mice with MR1 induction (FIG. 3A). In addition, the grafts are functioning on days 171 (n=2), 140 (n=4) and 120 (n=6) in diabetic NOD mice treated with a single agent, YTS199.7 (FIG. 3B). These results are important because they demonstrate that the double capsule can protect xenogeneic islets in diabetic NOD recipients treated with only a single agent, unlike the single capsule which required dual costimulatory blockade for long-term function of xenogeneic islets.

Figure 4:
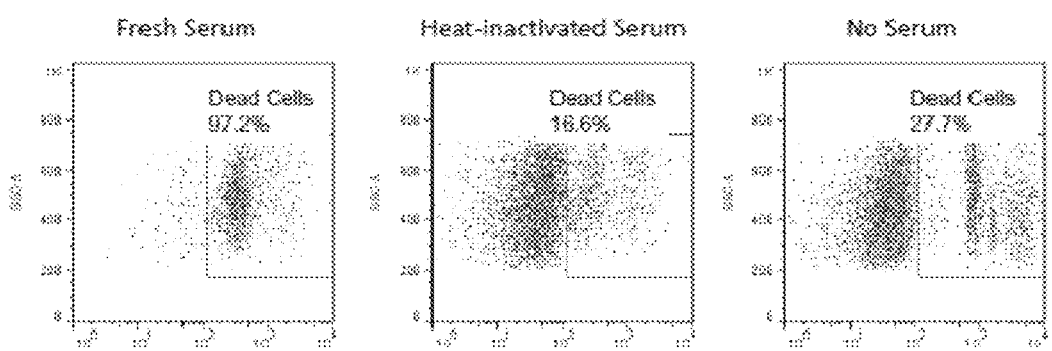
FIG. 4 shows results of a complement cytotoxicity assay. Fresh APIs were exposed to either fresh NHP serum, heat inactivated serum, or media without serum, stained with 7-AAD, and analyzed by flow cytometry.

Example 4: Double Encapsulation Protects Islets Against Damage by Non-Human Primate (NHP) Serum and Complement Non-human primate (NHP) serum damages free APIs when complement is active. APIs were treated for 15 minutes with either fresh NHP serum, heat inactivated serum, or media without serum. The cells were stained with the red 7-AAD stain (which binds to the DNA of membrane compromised cells and is used to measure cells killed by cytolytic activity). The cells were analyzed by flow cytometry, and dead cells were detected based on light scatter and uptake of 7-AAD. Fresh NHP serum lysed free APIs (97.2% cells), but heat-inactivated serum did not (FIG. 4). This data indicates that exposure to NHP serum results in islet killing and that lysis requires complement.

Figure 5:
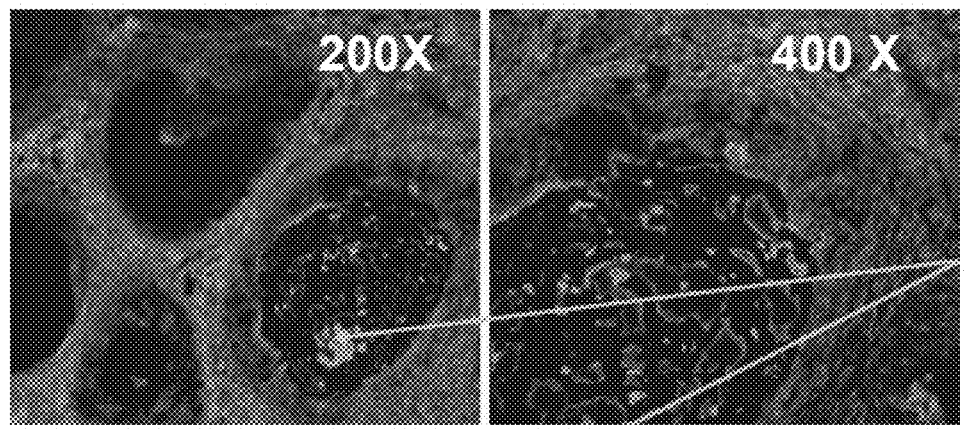
FIG. 5 shows images of NHP omentum and encapsulated islets stained with FITC-anti-primate IgG antibody by confocal microscopy.

IgG diffuses into standard barium-gelled LVM alginate capsules transplanted IP in NHPs. Frozen sections of capsules entrapped in the omentum biopsied from NHPs at necropsy were stained with dye (FITC)-conjugated anti-primate IgG and visualized by confocal microscopy. Primate IgG (green) can be seen on the omentum outside the capsules and also inside the capsules where APIs appear to have been lysed (FIG. 5).

Figure 6:
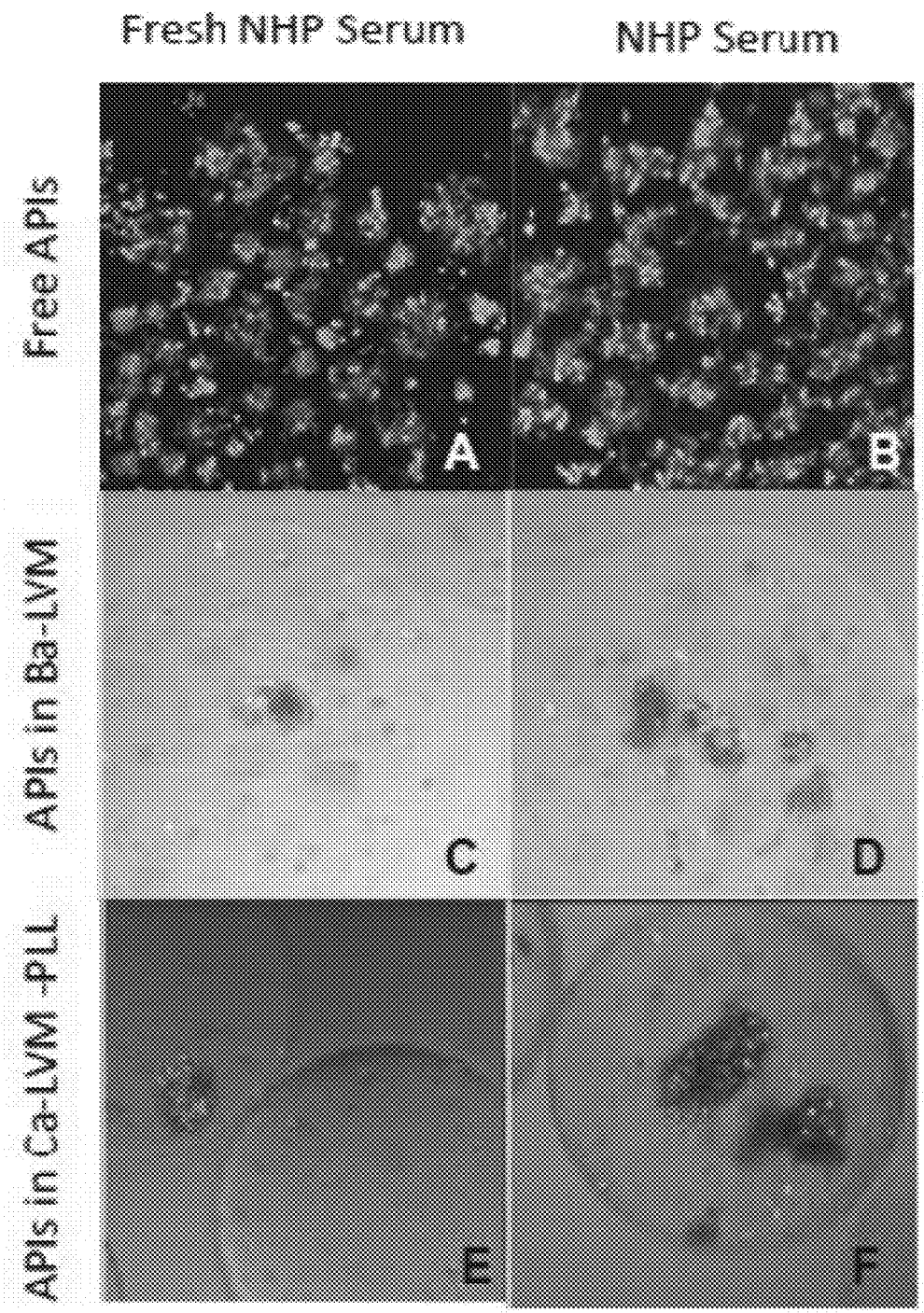
FIG. 6 shows pictures on the effect of NHP serum on free versus encapsulated APIs.

Encapsulation protects islets against damage by NHP serum and complement. Free APIs and encapsulated APIs were cultured in the presence of fresh NHP serum or heat-inactivated NHP serum for 24 hr. Then the free API and encapsulated APIs were stained with Calcein AM/EtBr to assess viability, and images were captured by confocal microscopy (exciting at 488 and 545 nm lasers). Fresh serum lysed free APIs, but heat inactivated serum inflicted no damage (FIGS. 6 A and B). Encapsulated APIs showed little, if any, serum-mediated damage over a 6-day period (FIGS. 6 C,D,E,F). These data indicate that complement plays a role in damage to free, non-encapsulated APIs by human or primate serum and that encapsulation can protect against this damage.

Example 5: Double Capsule is an Effective Barrier Against IgG

Figure 7:
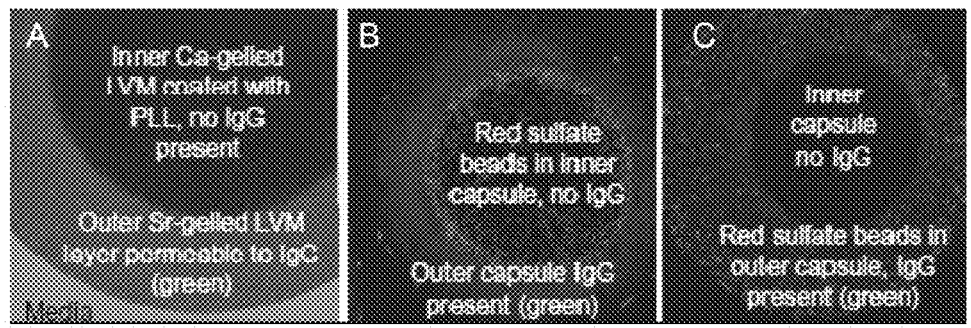
FIG. 7 shows data indicating IgG diffuses into the outer alginate layer of double capsules, but not into the PLL-coated, inner bead. Magnification 400×.

IgG can diffuse into the outer Sr-gelled LVM alginate layer of the double capsules relatively quickly, but IgG does not diffuse into the inner PLL-coated Ca-gelled LVM bead. When empty double capsules were incubated with FITC-labeled IgG for 24 hours and analyzed by confocal microscopy, IgG diffused into the outer alginate layer, but not into the inner, PLL-coated bead (FIG. 7A). High protein-binding red sulfate microspheres were placed in either the inner, PLL-coated Ca-gelled alginate or the outer, Sr-gelled alginate, and the capsules were exposed to FITC-IgG (green) for 23 hours. The presence of IgG was detected by a color change of the microspheres from red to green (FIGS. 7B and 7C).

Example 6: Local Release of Immunomodulatory Drugs

Figure 8:
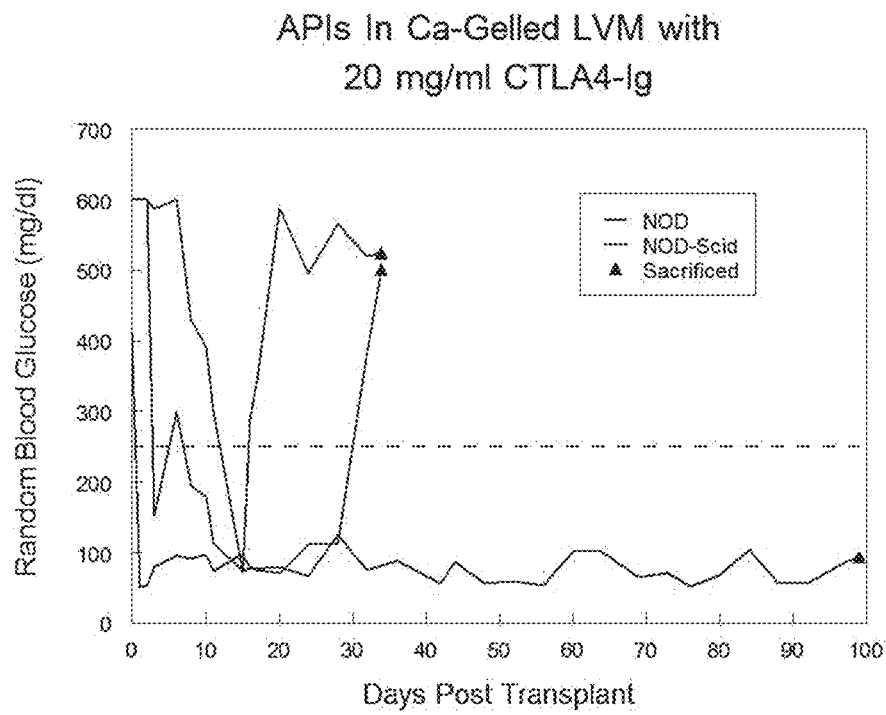
FIG. 8 data on the function of APIs implanted with alginate capsules containing 20 mg/mL CTLA4-Ig in NOD mice.
Figure 9:
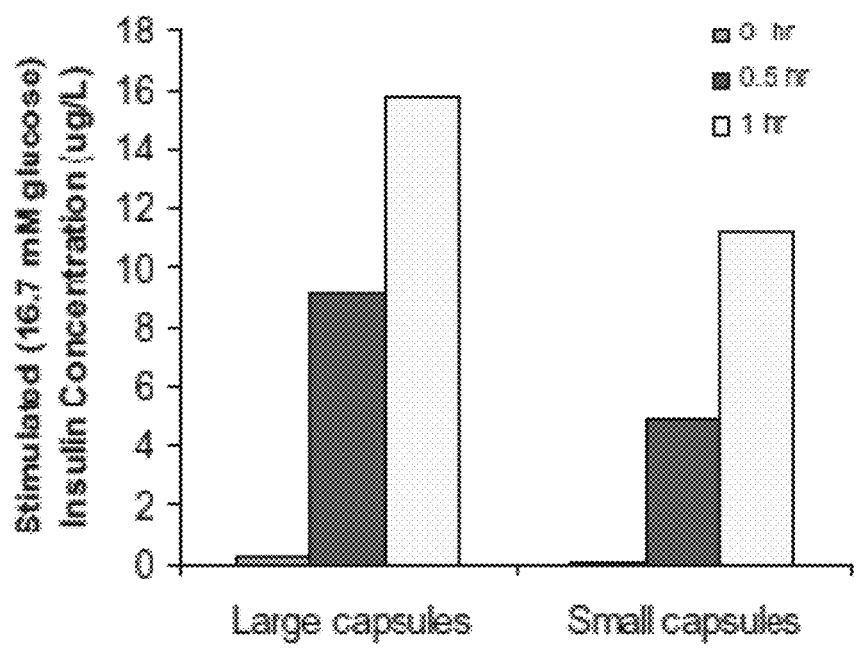
FIG. 9 shows data on the static glucose stimulated insulin release assay comparing APIs in small (400 μm) verses larger capsules (800 μm), Sr-gelled 2.8% LVM alginate.

The ability of CTLA4-Ig incorporated in alginate to prolong encapsulated islet xenograft function was tested. Diabetic NOD mice were transplanted with APIs encapsulated in Ca-gelled 3.2% alginate admixed with CTLA4-Ig (20 mg/ml). The grafts functioned for 99 days in 1 NOD-Scid, but the grafts were rejected at days 15 and 28 in two NOD mice (FIG. 8). CTLA4-Ig is secreted by Ad-CTLA4-Ig-transduced APIs and is released from capsules in vitro. Encapsulated Ad-transduced APIs functioned poorly in diabetic NODs, but they functioned well for 50+ days in SZN-diabetic NOD-Scid mice. Lack of function by both Ad-CTLA4-Ig-transduced APIs and APIs transduced with the empty adenoviral vector suggests that the adenovirus may be immunogenic in NODs.

Figure 12:
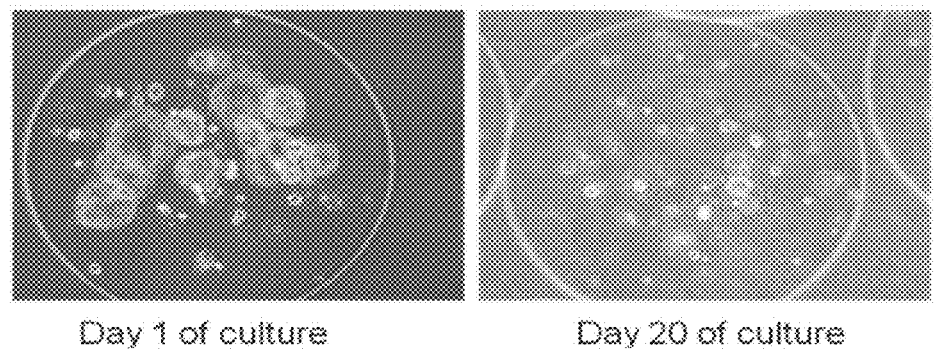
FIG. 12 shows MSC encapsulated with barium-gelled alginate.

Example 8: Mesenchymal Stem Cells (MSCs) in Barium-Gelled Alginate Microcapsules MSCs can be microencapsulated in Barium-gelled alginate, and they do not over-grow within the capsules in vitro (FIG. 12). Encapsulated API survived longer in 3 diabetic NOD mice when encapsulated MSCs were co-transplanted than without the MSCs.

Example 9: Chemical Cross-Linking

Figure 10:
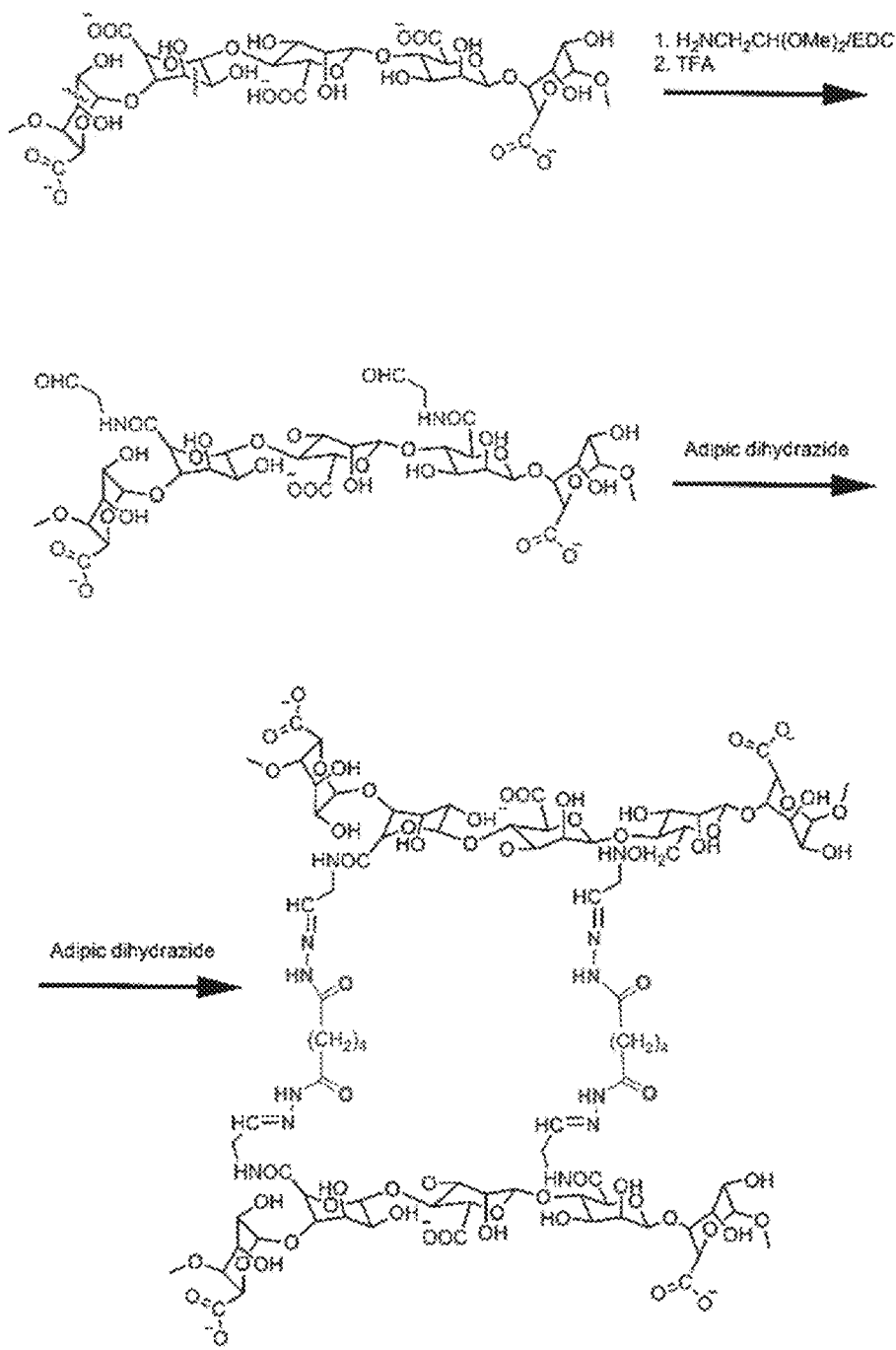
FIG. 10 shows a schematic illustration of crosslinking alginates.

One can crosslink aldehyde-modified alginate with diamines after ionic gelation. See FIG. 10. One activates the carboxylic groups on the alginate backbone using carbodiimide chemistry (water-soluble carbodiimide, 1-ethyl[dimethylaminopropyl]carbodiimide [EDC]/N-hydroxy succinimide [NHS]) and subsequently reacts with aminoacetaldehyde dimethylacetal (ADH). Removal of the acid-labile protecting groups yields the desired aldehydes. One crosslinks the alginate-aldehyde through both Schiff base and ionic bond formations.

Figure 11:
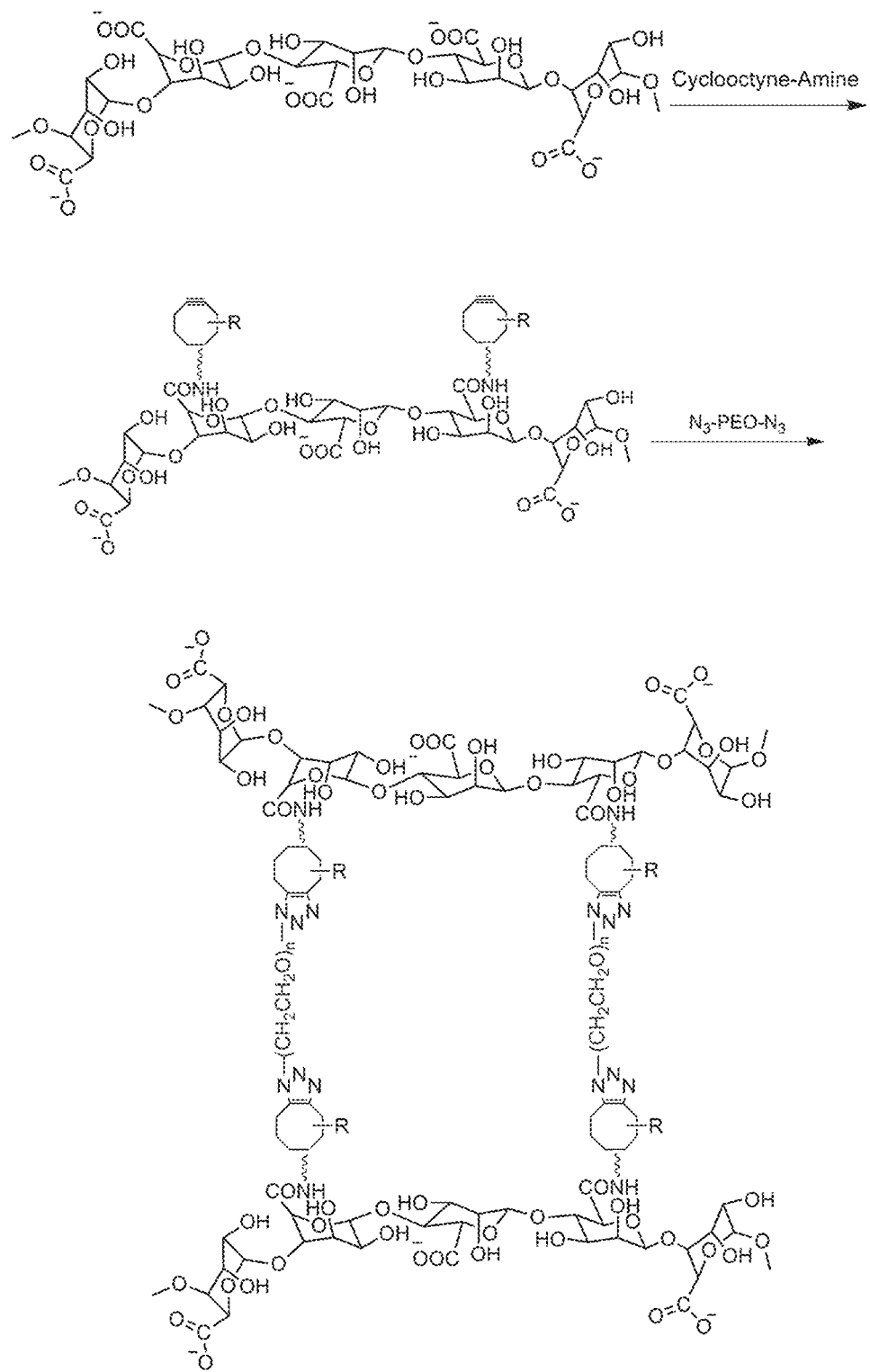
FIG. 11 shows a schematic illustration of crosslinking alginates.

In another contemplated embodiment, one crosslinks cyclooctyne derivitized alginates. See FIG. 11. One links alginate to cyclooctyne-PEG-amine with EDC. Cyclooctyne modified alginate may be chemically crosslinked with various diazide derivatives to generate crosslinked hydrogel triazoles (click chemistry). See Kolb et al., Angewandte Chemie, Int. Ed., 2001, 40(11): 2004-2014, hereby incorporated by reference in entirety.

What is claimed:

1. A double alginate layered capsule comprising:
   a) an islet cell;
   b) alginate;
   c) a calcium cation and a strontium cation; and
   d) a poly-L-lysine polymer;
   wherein the islet cell is surrounded by a first alginate layer wherein more than half of the monomer units are mannuronate comprising the calcium cation;
   wherein the first layer is surrounded by a second alginate layer comprising the strontium cation, a fusion protein composed of the Fc fragment of a human IgG immunoglobulin linked to the extracellular domain of CTLA-4, and an antibody that binds CD154; and
   wherein a poly-L-lysine layer comprises the poly-L-lysine polymer configured between the first and second layers;
   wherein the first layer is encapsulated by a process comprising,
      suspending the islet cell in 2.9% or greater but less than 3.5% of a low viscosity alginate wherein more than half of the alginate monomer units are mannuronate, providing an alginate mixture comprising the islet cell;
      gelling the mixture in a solution comprising the calcium cation providing a gelled inner capsule comprising the islet cell surrounded by a first alginate layer comprising the calcium cation wherein more than half of the alginate monomer units are mannuronate;
   wherein the second layer is encapsulated by a process comprising,
      mixing the gelled inner capsule with poly-L-lysine providing a poly-L-lysine layered capsule;
      suspending the poly-L-lysine layered capsule in 2% low viscosity alginate wherein more than half of the alginate monomer units are mannuronate providing an alginate mixture comprising the poly-L-lysine layered capsule; and
      gelling the alginate mixture comprising the poly-L-lysine layered capsule in a solution comprising the strontium cation providing a gelled outer capsule comprising the second alginate layer comprising the strontium cation wherein more than half of the alginate monomer units are mannuronate and configured such that the poly-L-lysine layer is between the first and second alginate layers.

2. The capsule of claim 1, wherein the diameter of the inner capsule is between 500 and 700 micrometers, and the diameter of the outer capsule is between 1000 and 1200 micrometers.

* * * * *